(12) United States Patent
Arbabian et al.

(10) Patent No.: US 10,856,740 B2
(45) Date of Patent: Dec. 8, 2020

(54) COHERENT FREQUENCY-DOMAIN MICROWAVE-INDUCED THERMOACOUSTIC IMAGING

(71) Applicant: The Board of Trustees of the Leland Stanford Junior University, Palo Alto, CA (US)

(72) Inventors: Mohammad Amin Arbabian, San Francisco, CA (US); Hao Nan, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 982 days.

(21) Appl. No.: 14/636,412

(22) Filed: Mar. 3, 2015

(65) Prior Publication Data
US 2016/0007859 A1    Jan. 14, 2016

Related U.S. Application Data

(60) Provisional application No. 61/947,259, filed on Mar. 3, 2014.

(51) Int. Cl.
*A61B 5/00* (2006.01)
*A61B 8/08* (2006.01)
(52) U.S. Cl.
CPC .............. *A61B 5/0093* (2013.01); *A61B 8/48* (2013.01)
(58) Field of Classification Search
CPC ....... A61B 5/0093; A61B 8/48; A61B 5/0051; A61B 5/0507; A61B 5/0035; A61B 8/485;
(Continued)

(56) References Cited

U.S. PATENT DOCUMENTS 61,104,942   8/2000   Kruger
6,567,688 B1  5/2003   Wang
(Continued)

OTHER PUBLICATIONS

Emerson, Jane et al. "Electromagnetic Acoustic Imaging". IEEE Transactions on Ultrasonics, Ferroelectrics and Frequency Control. vol. 60, No. 2, Feb. 2013: p. 364-372. (Year: 2013).*
(Continued)

*Primary Examiner* — Angela M Hoffa
*Assistant Examiner* — Helene Bor
(74) *Attorney, Agent, or Firm* — Lumen Patent Firm

(57) ABSTRACT

A thermoacoustic imaging device is provided having a transmitter configured to provide an electromagnetic transmit signal (e.g. a continuous sinusoidal signal) to an object being imaged. The transmit signal is a modulated continuous-wave signal based on a carrier frequency signal $f_c$ modulated at a modulation frequency at or near $f_m$. The detector is further configured to receive an acoustic signal from the object being imaged, and is responsive to acoustic frequencies at or near $2f_m$. A non-linear thermoacoustic effect in the object being imaged generates the acoustic signal from the object being imaged. Spectroscopic maps could be generated and imaged object could be analyzed. The device enhances signal-to-noise ratio of the reconstructed image and reduces the requirement of peak power in thermoacoustic imaging systems. In addition, the generated pressure of the imaged object is separated from microwave leakage and feedthrough in frequency through the nonlinear thermoacoustic effect.

18 Claims, 13 Drawing Sheets

(58) Field of Classification Search
CPC ......... A61B 5/7425; A61B 8/08; A61B 8/145; A61B 8/4416; A61B 8/4483; A61B 2562/0228
See application file for complete search history.

(56) References Cited

U.S. PATENT DOCUMENTS

| | | | | |
|---|---|---|---|---|
| 7,266,407 | B2* | 9/2007 | Li | A61B 5/0095 600/430 |
| 8,410,976 | B2* | 4/2013 | Szajnowski | G01S 13/282 342/118 |
| 9,000,974 | B2* | 4/2015 | Vacanti | G01S 13/10 342/118 |
| 2002/0035327 | A1* | 3/2002 | Kruger | A61B 5/0091 600/437 |
| 2006/0123884 | A1* | 6/2006 | Selker | G01N 21/1702 73/24.02 |
| 2007/0038060 | A1* | 2/2007 | Cerwin | A61B 5/05 600/407 |
| 2011/0040176 | A1* | 2/2011 | Razansky | A61B 5/0095 600/425 |
| 2011/0092824 | A1* | 4/2011 | Veen | A61B 5/14551 600/477 |
| 2015/0201838 | A1* | 7/2015 | Gencer | A61B 5/0051 600/430 |
| 2015/0366458 | A1* | 12/2015 | Kellnberger | G01N 29/2418 600/407 |

OTHER PUBLICATIONS

H. Cao et al. "Coherent detection of pulsed narrowband terahertz radiation" Appl. Phys. Lett. 88, 011101 (2006) (Year: 2006).*

Kellnberger et al. Second harmonic acoustic responses induced in matter by quasi continuous radiofrequency fields. Applied Physics Letters 103, 153706 (2013).

* cited by examiner

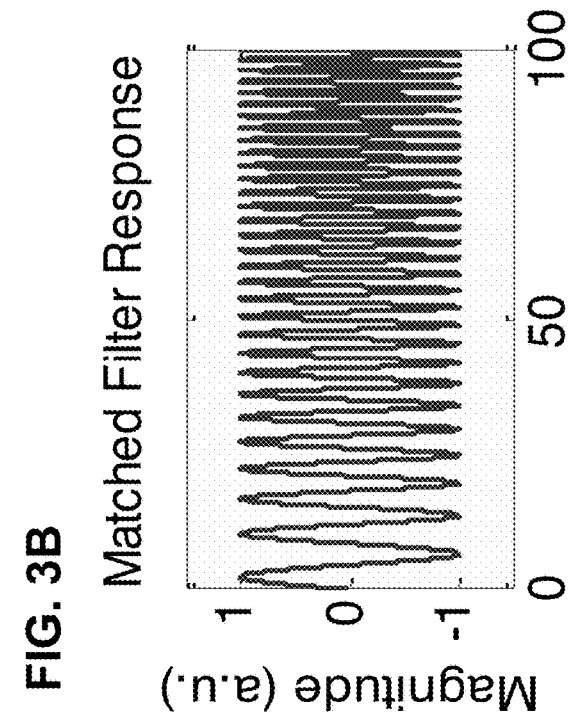
FIG. 3A Excitation Envelope Signal
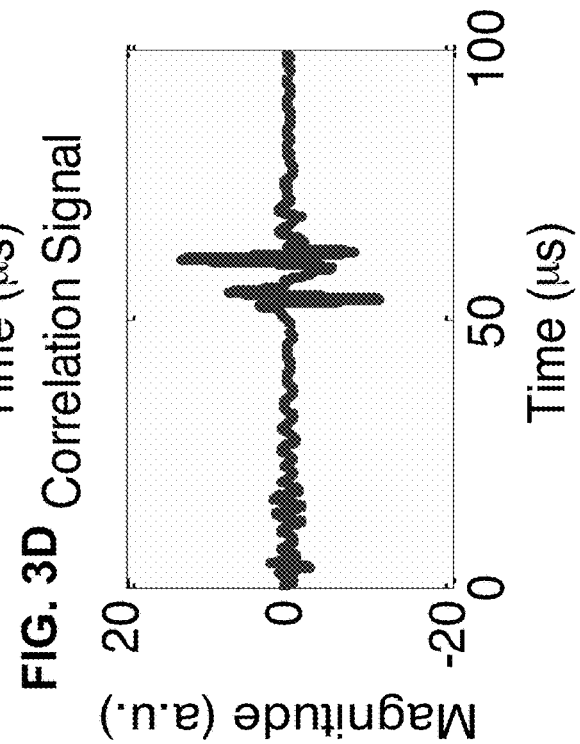
FIG. 3B Matched Filter Response
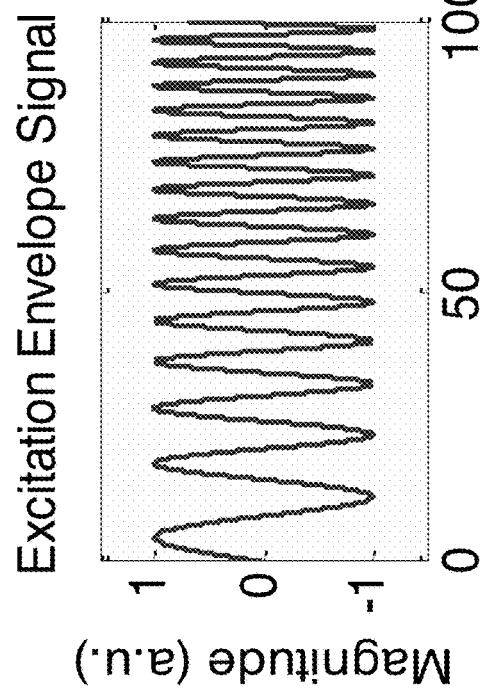
FIG. 3C Measured TA signal
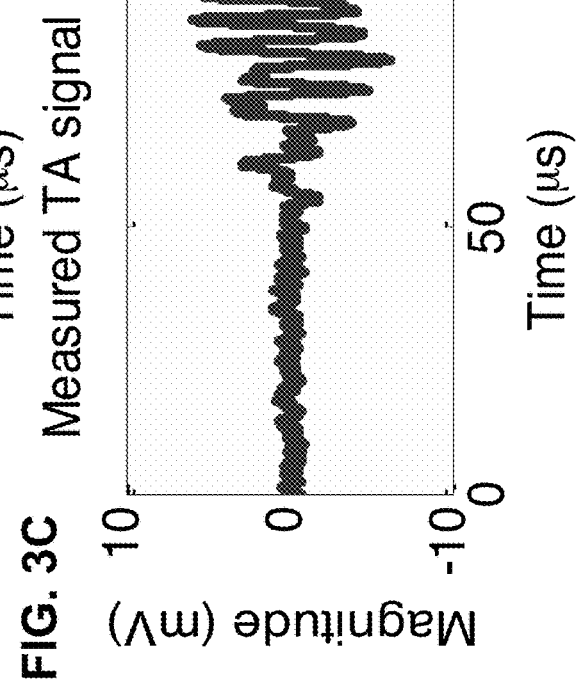
FIG. 3D Correlation Signal

FIG. 4A  Pulse TA Image
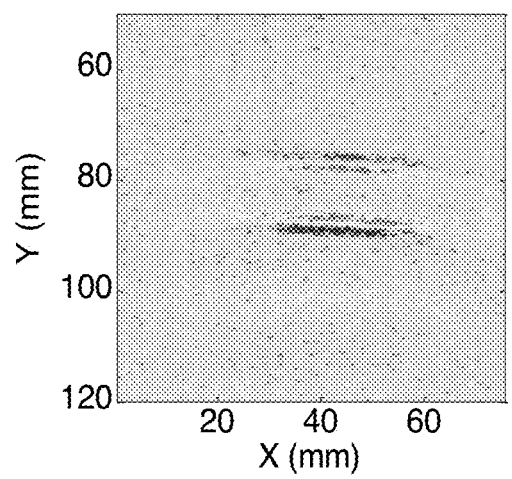
FIG. 4B  SFCW TA Image
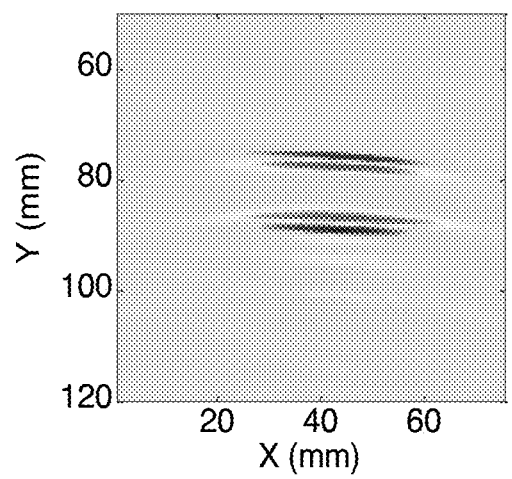
FIG. 4C  FMCW TA Image
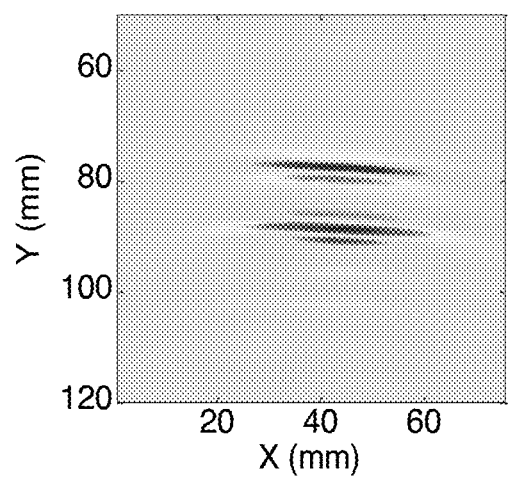

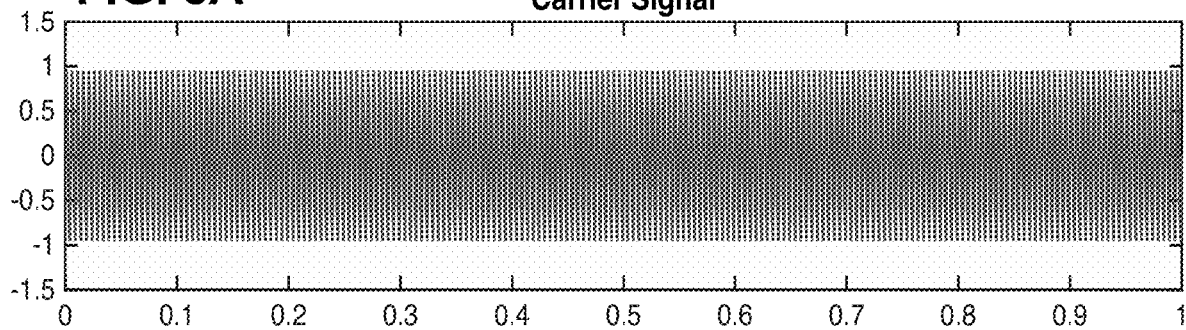
FIG. 5A Carrier Signal
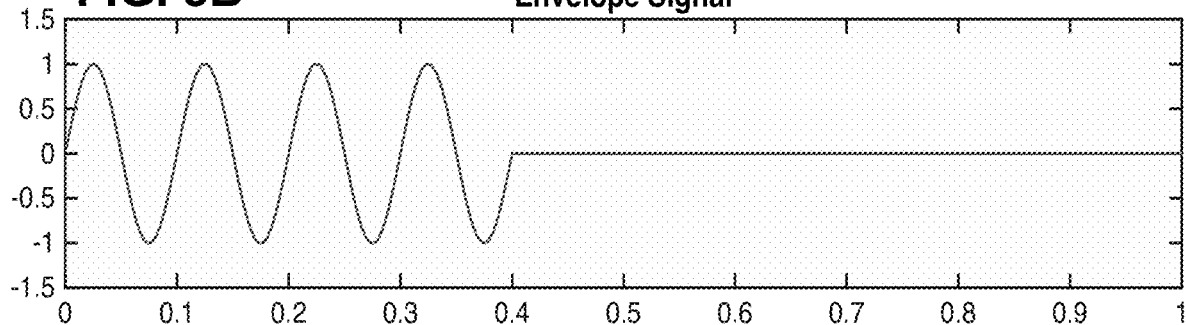
FIG. 5B Envelope Signal
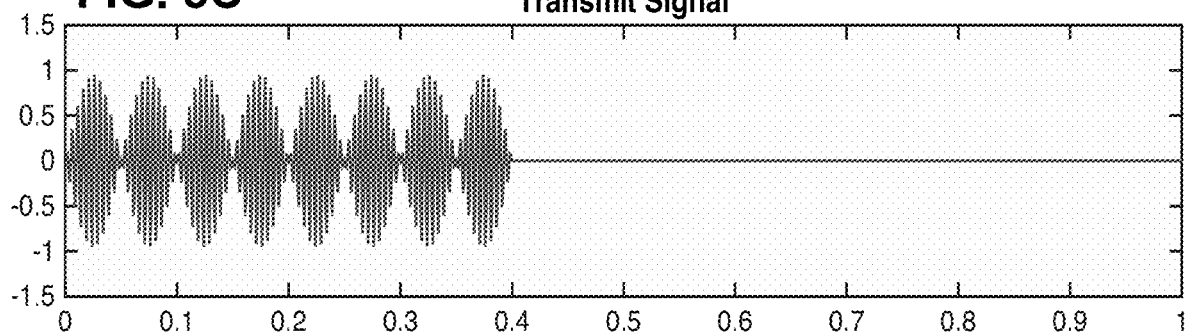
FIG. 5C Transmit Signal

COHERENT FREQUENCY-DOMAIN MICROWAVE-INDUCED THERMOACOUSTIC IMAGING

CROSS-REFERENCE TO RELATED APPLICATIONS

This application claims priority from U.S. Provisional Patent Application 61/947,259 filed Mar. 3, 2014, which is incorporated herein by reference.

STATEMENT OF GOVERNMENT SPONSORED SUPPORT

This invention was made with Government support under contract no. HR0011-13-C-0060 awarded by the Defense Advanced Research Projects Agency. The Government has certain rights in the invention.

FIELD OF THE INVENTION

The invention relates to medical imaging devices, methods and systems.

BACKGROUND OF THE INVENTION

The majority of the common imaging modalities currently used for diagnosis and screening rely on physical interaction concepts developed over 30 years ago. Conventional imaging systems often face substantial challenges in one or more of the following areas: safety (e.g. ionizing radiation), cost, size, and portability of the imaging device (e.g. in the case of MRI or CT scanners). In addition to addressing these concerns, a new imaging device will also need to consider conventional figures of merit: targeting contrast, resolution, and image quality.

Today, numerous medical applications will greatly benefit from a handheld imaging solution that provides sufficient contrast and resolution for detection of internal injuries and hemorrhages, identification of abnormal tissue (e.g., in widespread cancer screening), and other ambulatory care situations that need immediate and on-site access.

SUMMARY OF THE INVENTION

A thermoacoustic imaging device is provided addressing problems and shortcomings in the art. The device has a transmitter configured to provide an electromagnetic transmit signal (e.g. a continuous sinusoidal signal) to an object being imaged. The transmit signal is a modulated continuous-wave signal based on a carrier frequency signal $f_c$ modulated at a modulation frequency at or near $f_m$. In one example, $f_c$ is in the range of 100 MHz to 300 GHz and $f_m$ is in the range of 20 kHz~100 MHz. The detector is further configured to receive an acoustic signal from the object being imaged, and is responsive to acoustic frequencies at or near $2f_m$. A non-linear thermoacoustic effect in the object being imaged generates the acoustic signal from the object being imaged.

The modulation could take various forms. In one example, the modulation signal is a continuous modulation signal or an interrupted modulated continuous-wave signal. A mixer could be used for obtaining such a continuous modulation signal. In another example, the modulation signal is an interrupted modulation signal. A switch could be used for obtaining such an interrupted modulation signal.

In yet another example, the modulation signal is a double-sideband fully suppressed-carrier modulation, which is obtained by multiplying the carrier signal $f_c$ with modulation signal $f_m$.

In still another embodiment, the modulation signal could involve a form of pulse modulation. The pulse modulation is bipolar and a double side-band fully suppressed-carrier modulation.

In still another example, the electromagnetic transmit signal could be modulated at one or more further frequencies distinct from $f_m$.

The thermoacoustic imaging device could be configured for other tasks. In one example, the device could be configured to include a processing device for signal conditioning, leakage and feed-through suppression, coherent signal processing, or image reconstruction.

In another example, the device could be configured to include a filtering device with a cutoff frequency in between $f_m$ and $2f_m$. The filtering device suppresses transmit microwave leakage and feedthrough to the detector, where their frequencies are around $f_m$. The detected $2f_m$ pressure signal would pass through the device without filtering.

In still another example, the device could be configured to include a matching network for impedance matching of the transmit signal. The equivalent input complex impedance of the object being imaged could be dynamically matched with an output complex impedance of the transmit device to maximize power transmission and minimizing power reflection. The complex impedance is defined as the complex electronic impedance. Since the modulation signal could be at multiple frequencies or in a frequency range, the impedance matching network could be dynamically adjusted to optimize impedance matching for each frequency.

In still another example, the device could be configured to include a coherent detection sub-system such that the modulation of the electromagnetic transmit signal is derived from a transmit frequency reference at $f_m$. The receiver frequency reference at $2f_m$ could be generated from the transmit frequency reference via a second-order nonlinearity, and the coherent detection of the acoustic signal could be performed using the receiver frequency reference or the coherent detection could include the use of a phase locked loop.

In still another example, the device could be configured to frequency sweep the modulation frequency $f_m$ and the carrier frequency $f_c$ for generating a two-dimensional spectroscopic map of the imaged object.

In still another example, the device could be configured to include a processor to analyze the imaged object.

In still another example, the device could be configured to include a processor configured for frequency correction of the received acoustic signal, calibration of the detector, or equalization of the received acoustic signal to compensate non-idealities in a frequency response of the detector.

Frequency domain correction and equalization could be applied to the received signal to correct for any non-idealities in the chain, including, but not limited to, the finite and non-ideal frequency response of the transducer, the media, and the detection circuitry. Such a system would correct for both amplitude and phase of the received signal and uses several parameters (e.g. input signal and envelope) for input to the correction unit.

In view of the embodiments described herein, one of the advantages is that significant signal-to-noise (SNR) improvements can be achieved by the coherent processing techniques. Embodiments of this invention could also be advantageous to significantly reduce the required peak RF power levels from the transmitter. Such advantages, result in smaller and more efficient devices and systems, opening up the way for handheld and battery operated operation of medical imagers. In addition, larger energy can be deposited to improve SNR of the reconstructed image. Additionally, embodiments of the invention are not limited by stress confinement and thermal confinement, where they would limit the maximum energy deposit of pulsed thermoacoustic method and they would limit the SNR of the reconstructed image. By improving SNR, embodiments of this invention reduce the requirement of peak power in thermoacoustic imaging and enable a full solid-state implementation of the device/system. It also enables a portable and handheld thermoacoustic system, while pulsed thermoacoustic usually requires a bulky, expensive vacuum source. Using a double-sideband suppressed-carrier modulation and nonlinear thermoacoustic effect, the generated pressure is separated with microwave leakage and feedthrough in frequency, which enables filtering the latter components by a low-pass filter.

BRIEF DESCRIPTION OF THE DRAWINGS

FIGS. 3A-D show according to an exemplary embodiment of the invention in FIG. 3A the excitation envelope (chirp) signal, in FIG. 3B a matched filter response, in FIG. 3C a measure thermoacoustic (TA) signal, and in FIG. 3D a correction signal.

FIGS. 4A-C show according to an exemplary embodiment of the invention images from a chicken breast with 11 mm thickness, where in FIG. 4A is based on a pulsed thermoacoustic (TA), in FIG. 4B is based on a stepped-frequency continuous-wave (SFCW) thermoacoustic (TA), and in FIG. 4C is based on a frequency-modulated continuous-wave (FMCW) thermoacoustic (TA).

FIGS. 5A-C show a partly suppressed transmit signal, or interrupted continuous modulation signal, according to an exemplary embodiment of the invention. FIG. 5A shows a carrier signal, FIG. 5B shows an envelope signal being suppressed the latter part of the signal, and FIG. 5C shows the transmit signal, which is the carrier signal multiplied with the partly suppressed envelope signal or interrupted continuous modulation signal. It is noted that this signal can be repeated.

FIG. 6A shows a frequency response of the detector. FIG. 6B shows a frequency spectrum of a generated pressure. FIG. 6C shows a frequency spectrum of received signal after detector. The frequency spectrum of the received signal after the detector is product of frequency spectrums of the detector and the generated pressure. FIG. 6D shows a reconstructed frequency spectrum after frequency correction and equalization. The frequency spectrum after correction and equalization is similar to frequency spectrum in FIG. 6B. Both amplitude and phase are corrected and equalized.

DETAILED DESCRIPTION

Figure 1:
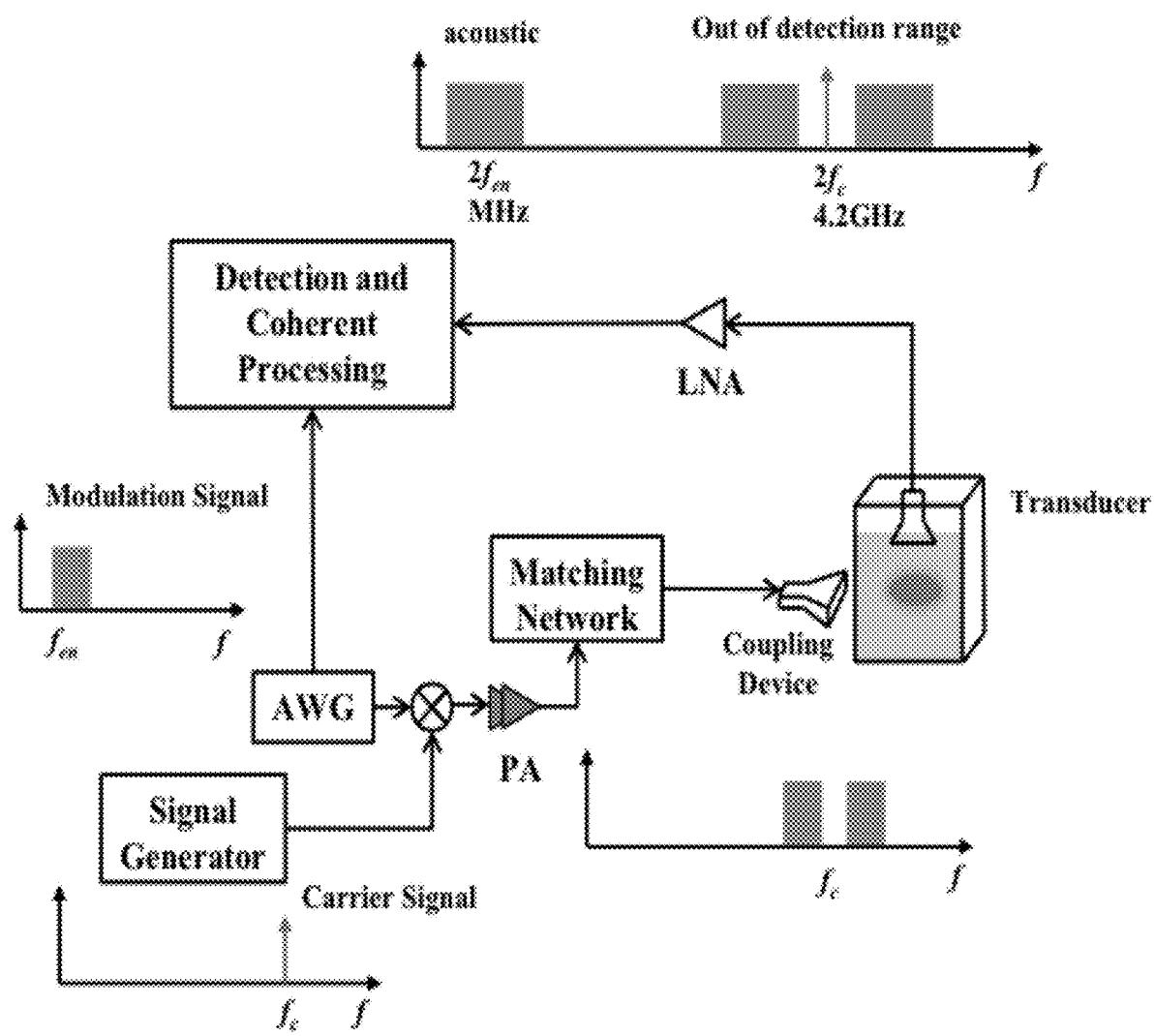
FIG. 1 shows a schematic representation of the thermoacoustic imaging device according to an exemplary embodiment of the invention. In this example, an arbitrary wave generator (AWG) generates an envelope signal and modulates the carrier signal.

The thermoacoustic (TA) effect was first demonstrated by using a pulse light source incident on a sample to generate acoustic waves. Using microwave (MW) excitation, the microwave-induced thermoacoustic technique combines the contrast of microwave imaging, which is based on dielectric properties of different materials, with the high resolution of ultrasound (US) detection. It has the potential to achieve penetration depth in excess of 5 cm even in dispersive tissue. With this technique, the target tissue generates stress wave due to thermal expansion after the absorption of the microwave energy. Photoacoustic imaging, which employs laser as the excitation source, shares the same physical principles. However, it is only suitable for superficial applications because of the limited penetration depth.

Conventional microwave-induced thermoacoustic uses a high power source to generate a short pulse. The stress confinement condition limits the maximum pulse width. To achieve the required signal to noise (SNR) levels a higher pulse energy is required, and therefore, with a limited pulse width, the peak transmit power is increased and usually exceeds several kW in the microwave regime.

In addition to requiring bulky and expensive vacuum sources (klystron or magnetron), this may also cause safety issues. In this invention, we provide and successfully demonstrate coherent frequency domain signaling and provide examples in the form of microwave-induced thermoacoustic stepped-frequency continuous-wave (SFCW) and frequency-modulated continuous-wave (FMCW) approaches. The FMCW technique reduces the requirement for peak power by increasing pulse duration and takes advantage of a match-filtering receiver to achieve significant SNR improvement. Exemplary embodiments of the invention could be fully implemented with solid-state electronics and opens the way to a new generation of portable hand-held and even battery-operated medical imaging devices. The small capture time also enables the possibility of real-time imaging with a transducer array.

Implementation

SFCW and FMCW signaling techniques are commonly used in radar. Instead of sending a short pulse, the SFCW technique embodied in this invention sends continues wave signals in several discrete frequencies and synthesizes the frequency spectrum of the target impulse response. The SFCW system is inherently narrowband, which reduces the cost of the system implementation.

FMCW uses linear frequency modulation (LFM) microwave to excite the tissue. A matched filter algorithm could be used for post processing and greatly improves SNR levels. The SNR improvement is proportional to $\sqrt{m}$ with $m=(f_2-f_2)\times\tau$ being the time-bandwidth product. Here, $f_1$ and $f_2$ are the starting and ending frequency of the LFM signal and $\tau$ is the pulse width. The interrupted version of FMCW uses short microwave pulses to avoid the overlap and leakage between TX and RX. This approach has a large "blind range", which equals to the overall TX pulse width multiplied by speed of sound in tissue. Also, the small time-bandwidth product limits the SNR improvement level. In our approach, we use the long-pulse CW by reducing the leakage signal in the front-end and through that we achieve a significantly higher SNR improvement.

The generation of thermoacoustic signal follows the equation $$\left(\nabla^2 - \frac{1}{v^2}\frac{\partial^2}{\partial t^2}\right)p(r,t) = -\frac{\beta}{C}\frac{\partial Q(r,t)}{\partial t} \quad (1)$$

Here, p(r,t) is the stress at position r and time t, $v_s$ is the speed of sound, $\beta$ is the thermal expansion coefficient, C is the specific heat capacity, and Q(r,t) is the heating function, defined as thermal energy absorbed per unit time and unit mass. EQ. (1) describes the generation of pressure waves from a heat source. Q(r,t) can be written as $$Q(r,t)=\sigma E^2(r,t)+2\pi f\varepsilon_0\varepsilon'' E^2(r,t)+2\pi f\mu_0\mu'' H^2(r,t) \quad (2)$$

The first term is the conductivity loss, which is the dominant component in thermal energy generation in tissue. In tissue, permeability can be neglected. So heating function is proportional to $E^2(r,t)$.

To achieve frequency-domain imaging two problems need to be addressed. First, we need to show that signals remain fully coherent across the input (microwave) and output (US) domains. Radar works in a single microwave domain and this is automatically achieved whereas this is less trivial for our imager. Second, microwave excitation is in the GHz frequency range and US is in MHz. To apply coherent processing techniques we need the same modulation frequencies on both sides. This problem can be solved by applying the modulation to an envelope signal, which is later placed on the microwave carrier (2.1 GHz in this example, but could be anywhere in the RF to millimeter-wave frequency range, as shown in FIG. 1.

The microwave signal is a single tone envelope ($E_0 \cos(2\pi f_m t)$) modulated with carrier frequency $f_c$. Therefore, $$Q(r,t) \propto E_0^2 \cos^2(2\pi f_m t)\cos(2\pi f_c t) = 0.25 E_0^2 (1+\cos(4\pi f_m t))(1+\cos(4\pi f_c t)) \quad (3)$$

Therefore the TA signal will have the response at the frequency $2f_m$. The carrier frequency is in GHz range, which is beyond the transducer response and cannot be detected. In general, if the envelope signal has a frequency of $f_m$, the TA signal will have a frequency response at $2f_m$.

For FMCW, the excitation envelope signal is a LFM signal $\sin(2\pi(f_0+bt)t)$, with b the frequency sweep rate and $f_0$ the starting frequency. The heating function and the TA signal will follow $\sin(4\pi(f_0+bt)t)$ and the frequency of the matched-filter response is at twice the LFM frequency.

Experimental Results

For comparison, the experiments have been performed with an incoherent pulse method as well as a coherent frequency domain method. The schematic is shown in FIG. 1. An arbitrary wave generator (AWG) generates the low frequency envelope signal that modulates a 2.1 GHz carrier. A GaN PA is designed to bring peak power up to 120 W (for pulse operation). The average power remains below 12 W. This power is then coupled to the container without direct contact. The tissue sample is placed in the oil-filled container.

In this experiment, for detection, an immersion piezoelectric transducer at 0.5 MHz was used. A low noise amplifier (LNA) was employed for conditioning. After the low pass filter, the signal was averaged and sampled by the oscilloscope. A linear stage setup is used to perform a B-Scan to get the image. A piece of chicken breast was used as the imaging sample.

Figure 2A:
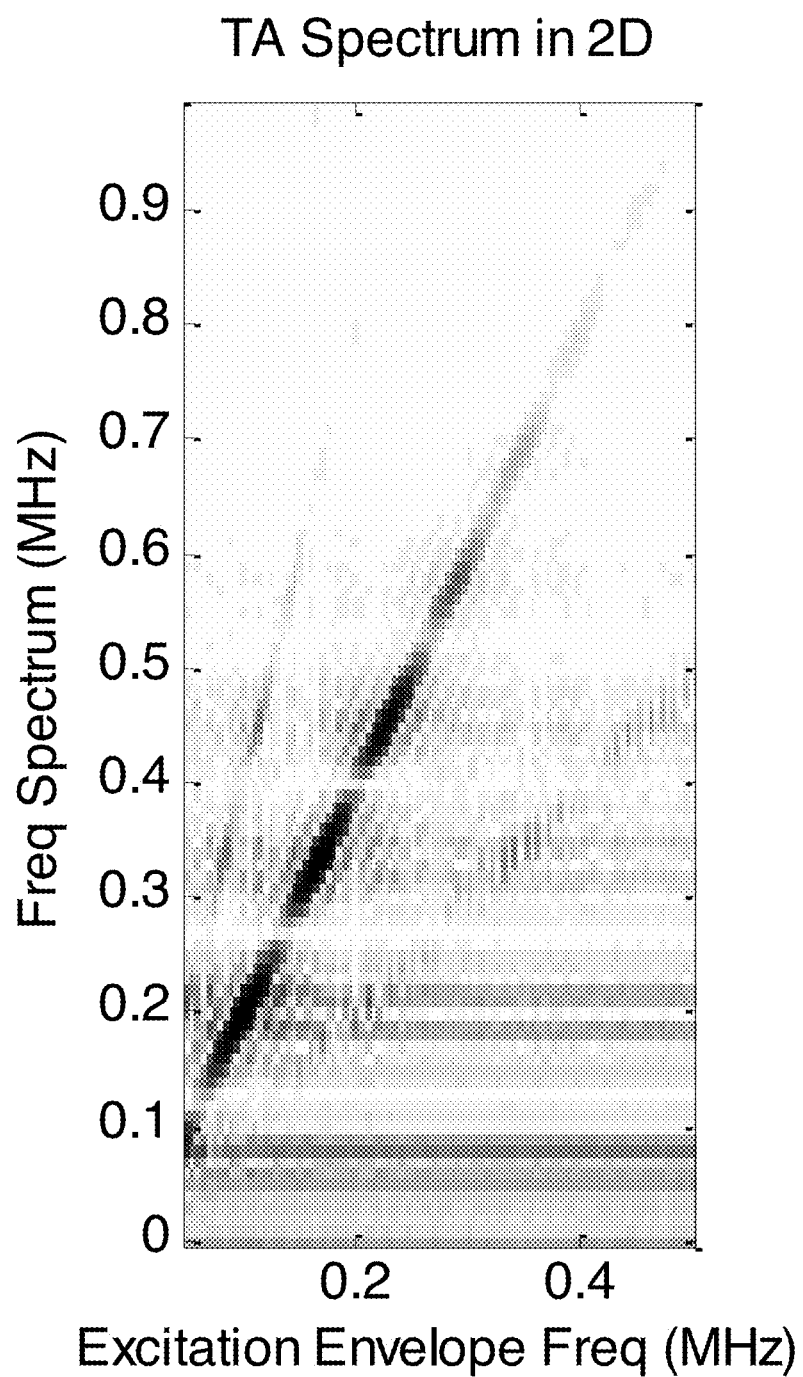
FIG. 2A shows the relation of a thermoacoustic (TA) spectrum and an excitation envelope frequency according to an exemplary embodiment of the invention.
Figure 2B:
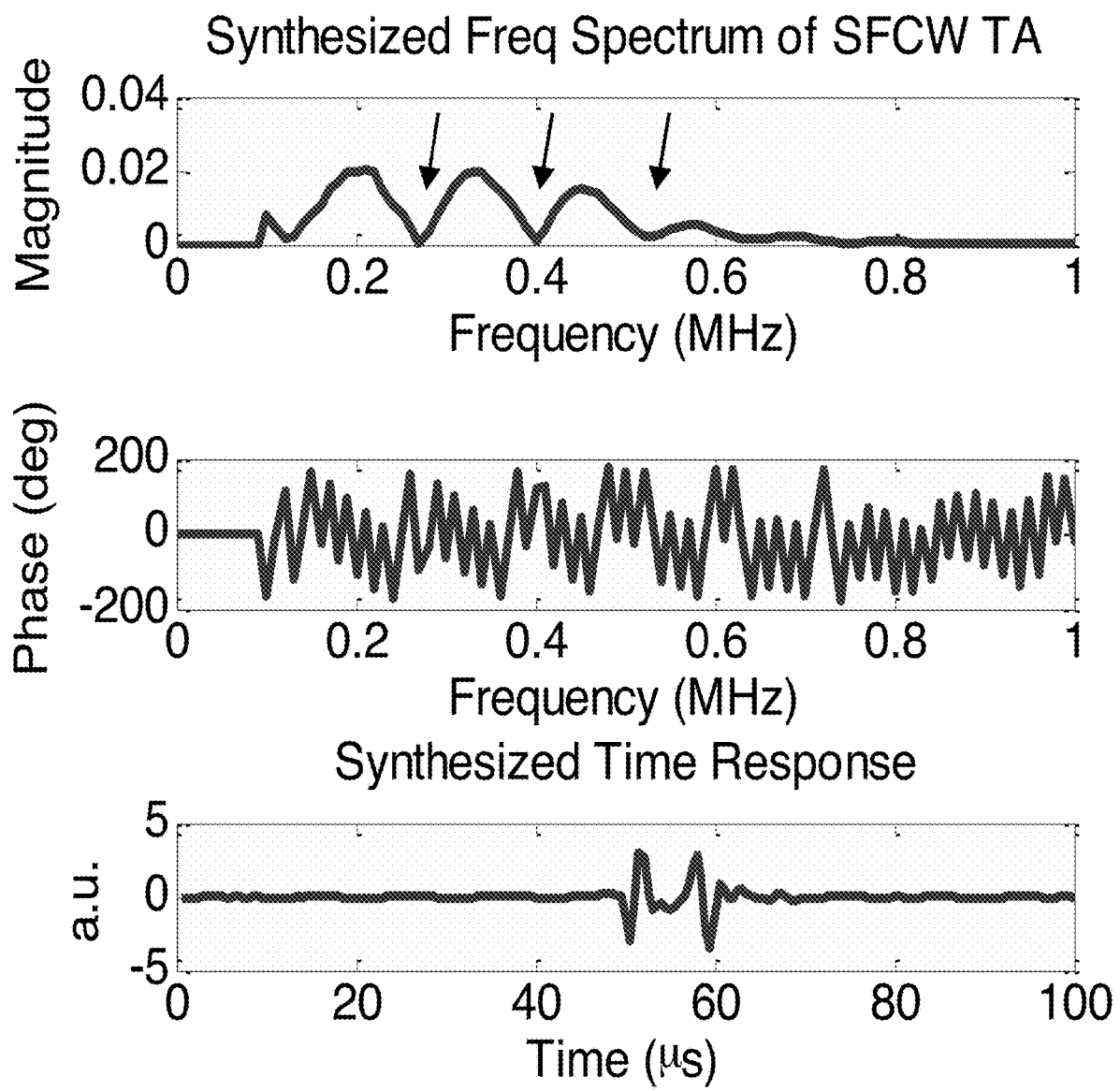
FIG. 2B shows a synthesized frequency spectrum (magnitude and phase) of a thermoacoustic (TA) signal. Arrows indicate the valleys, due to destructive interference. The final synthesized time response is plotted (bottom plot) with arbitrary unit (a.u.) according to an exemplary embodiment of the invention. The two interfaces of the imaged object are shown as two bipolar signals in the synthesized time response.
Figure 2C:
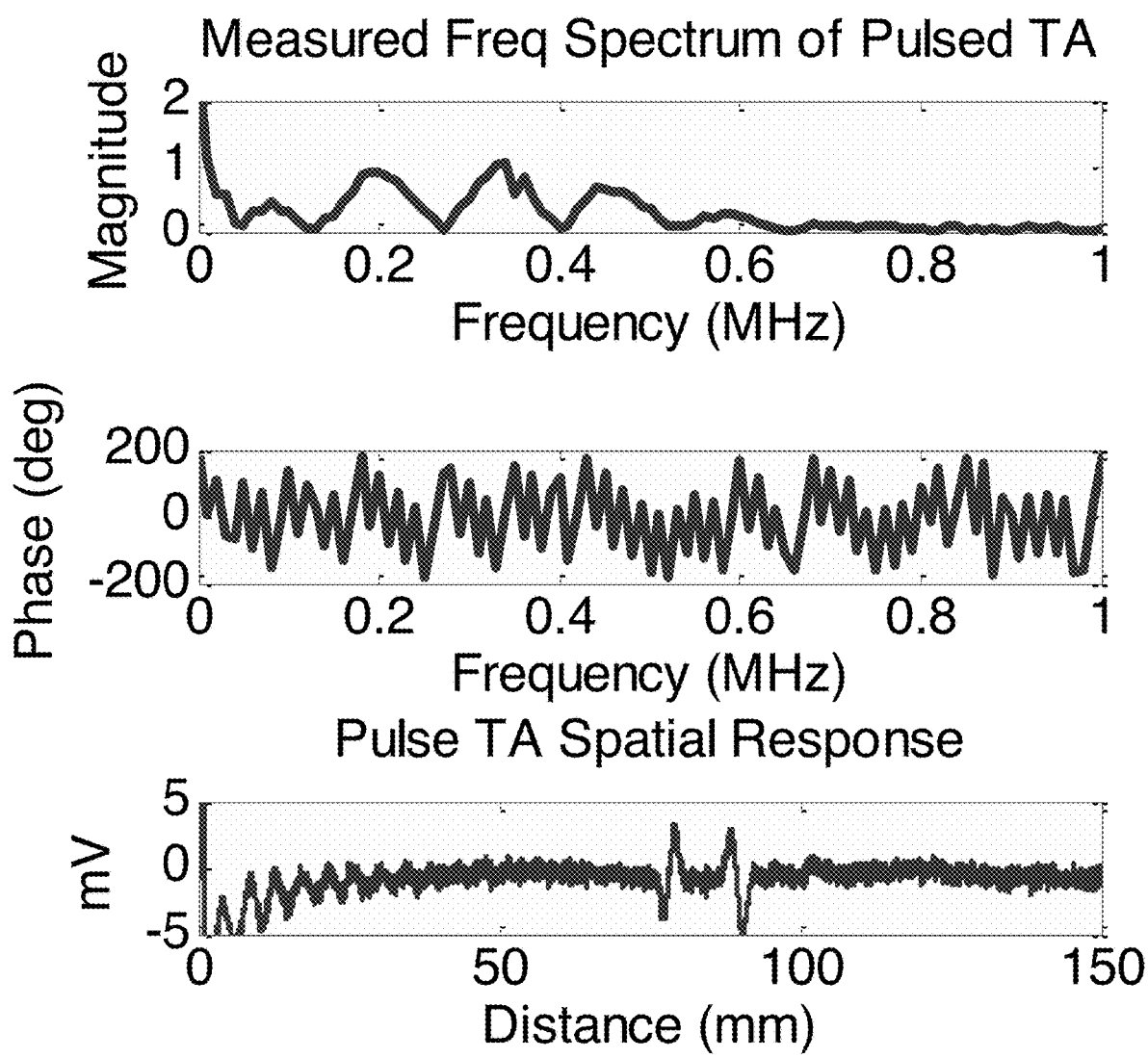
FIG. 2C shows a measured frequency spectrum and spatial response with pulsed thermoacoustic (TA) imaging according to an exemplary embodiment of the invention.
Figure 6A:
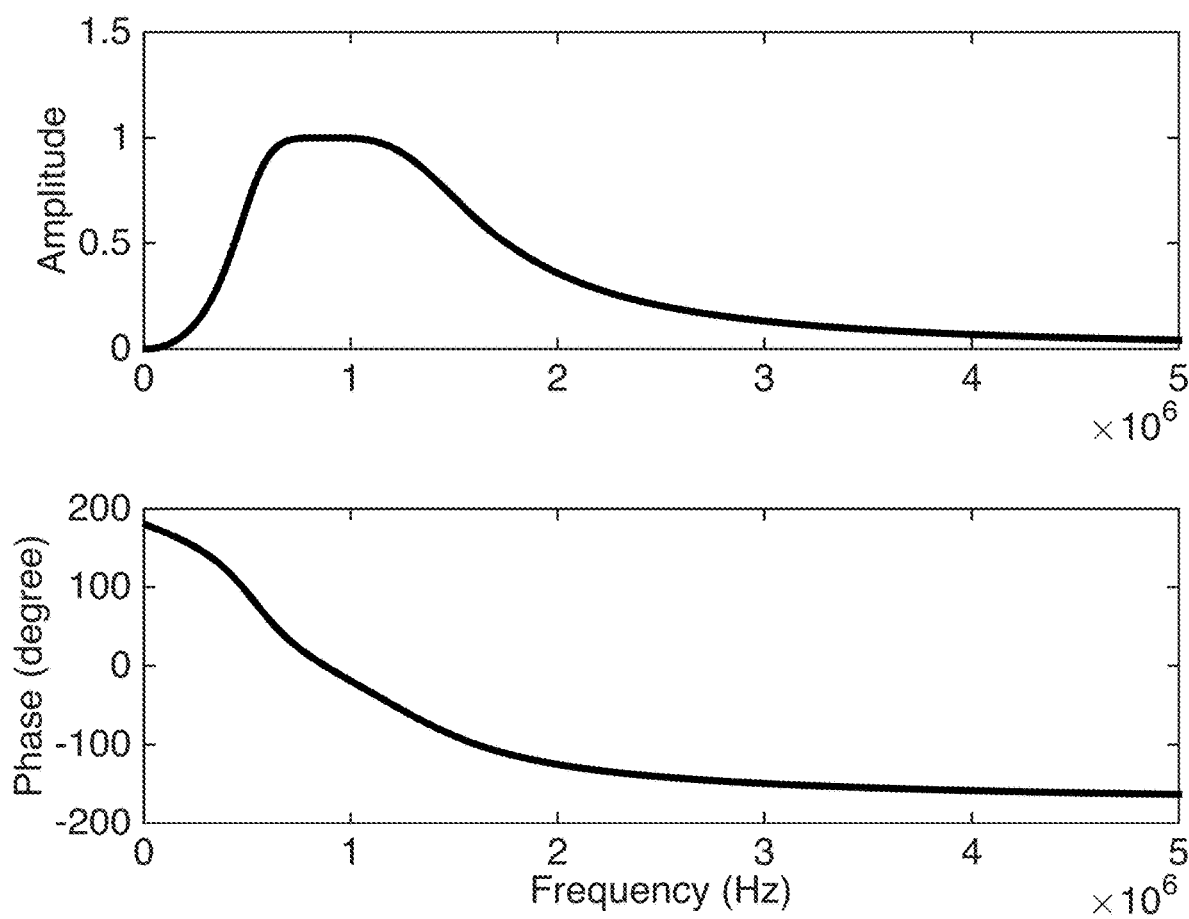
FIGS. 6A-D show an example frequency correction and an equalization of received signal according to an exemplary embodiment of the invention.
Figure 6B:
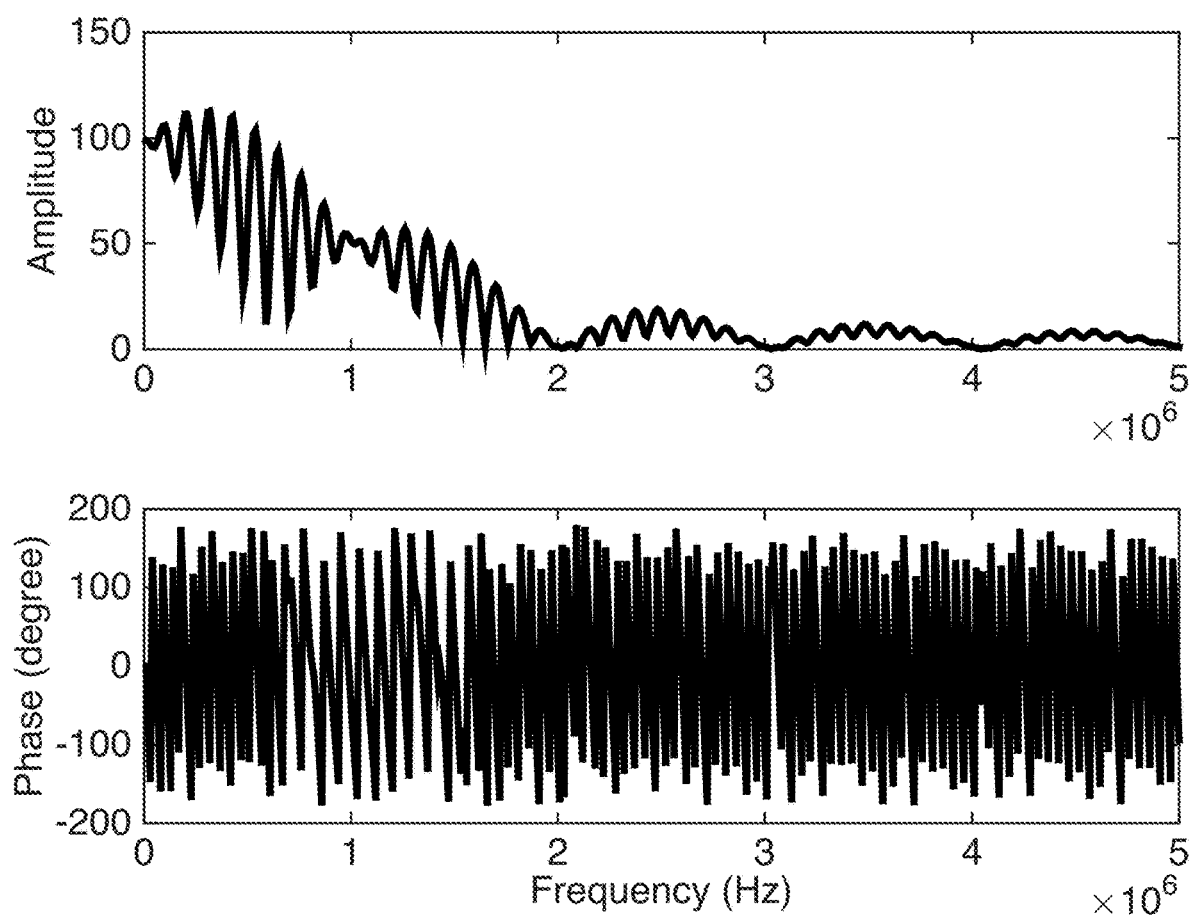
Figure 6C:
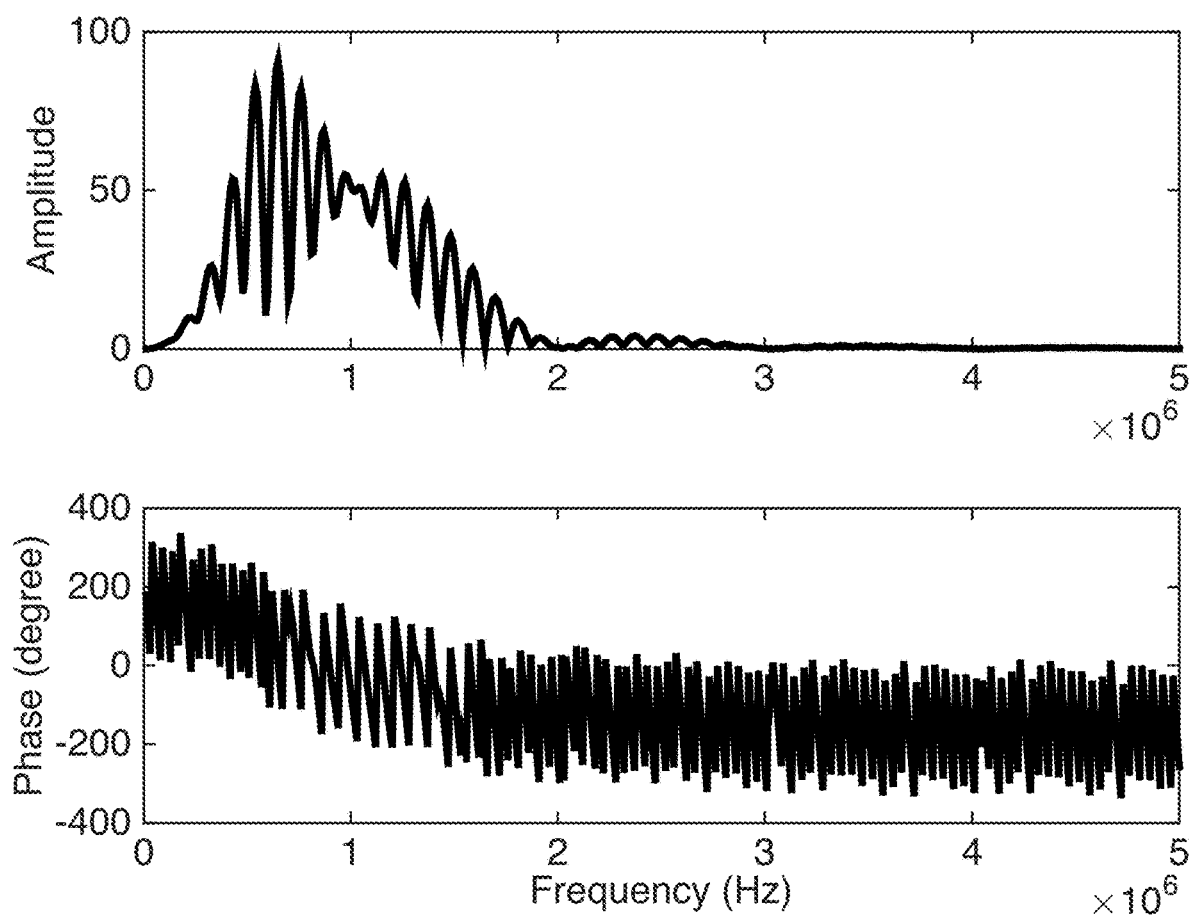
Figure 6D:
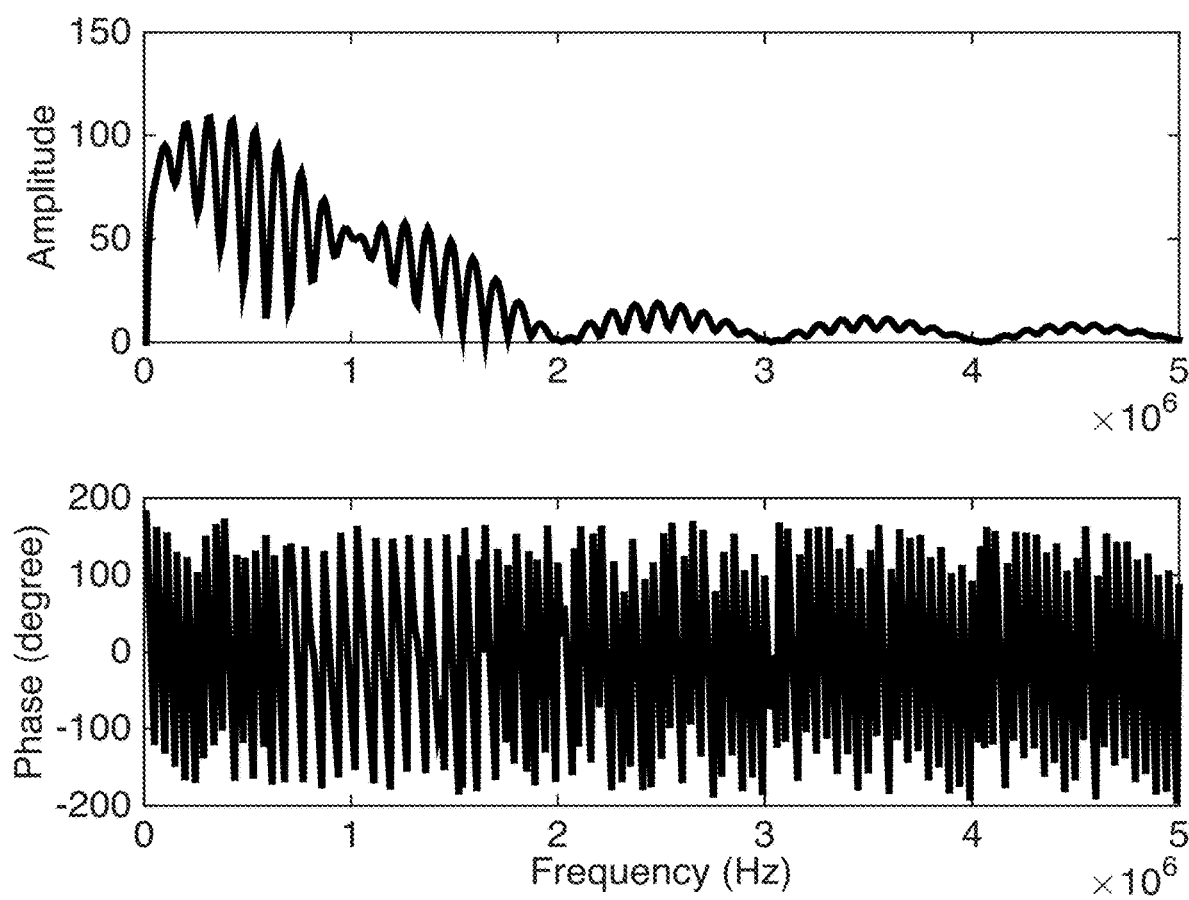
Figure 7:
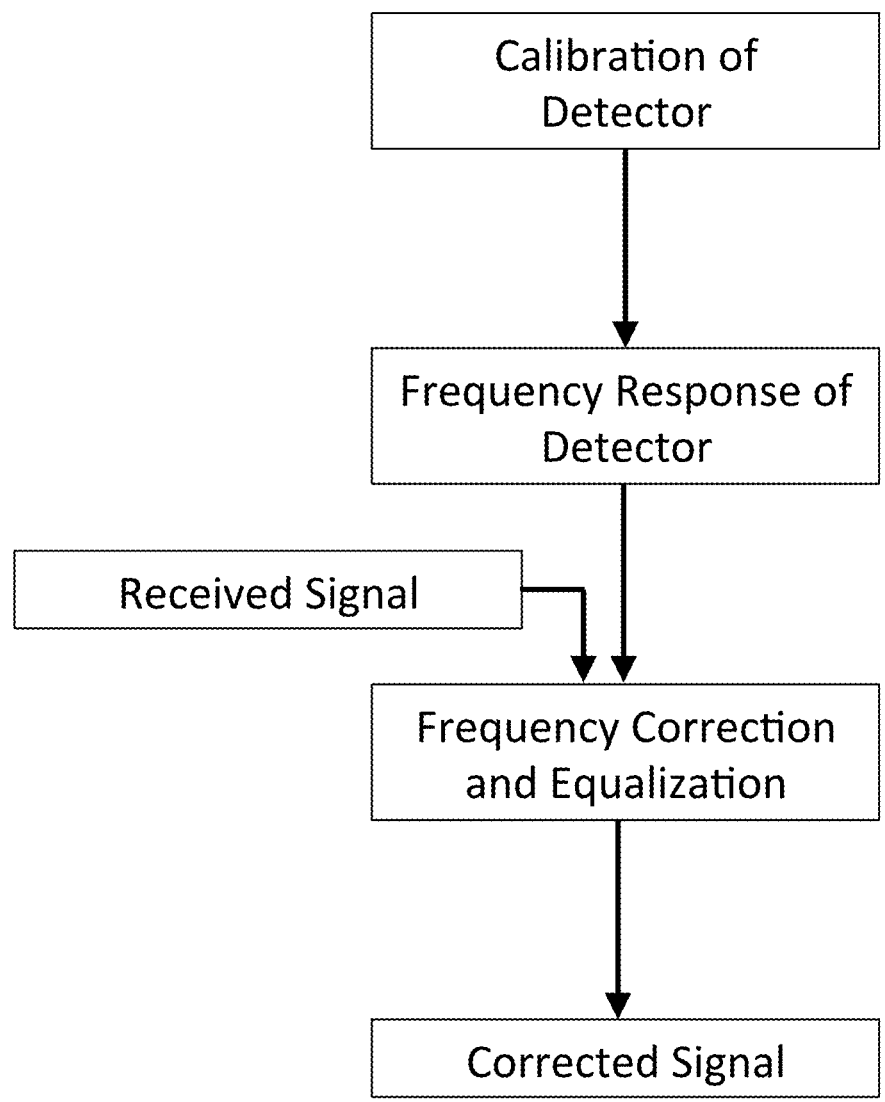
FIG. 7 shows according to an exemplary embodiment of the invention a block diagram of using frequency calibration, correction and equalization of the received signal. The calibrated frequency response of a detector could be used to correct and equalize the received signal, usually by dividing the frequency spectrum of received signal by frequency response of detector. The corrected time domain signal could be obtained by using inverse Fast Fourier Transform (FFT) of the corrected frequency spectrum of the received signal.
Figure 8:
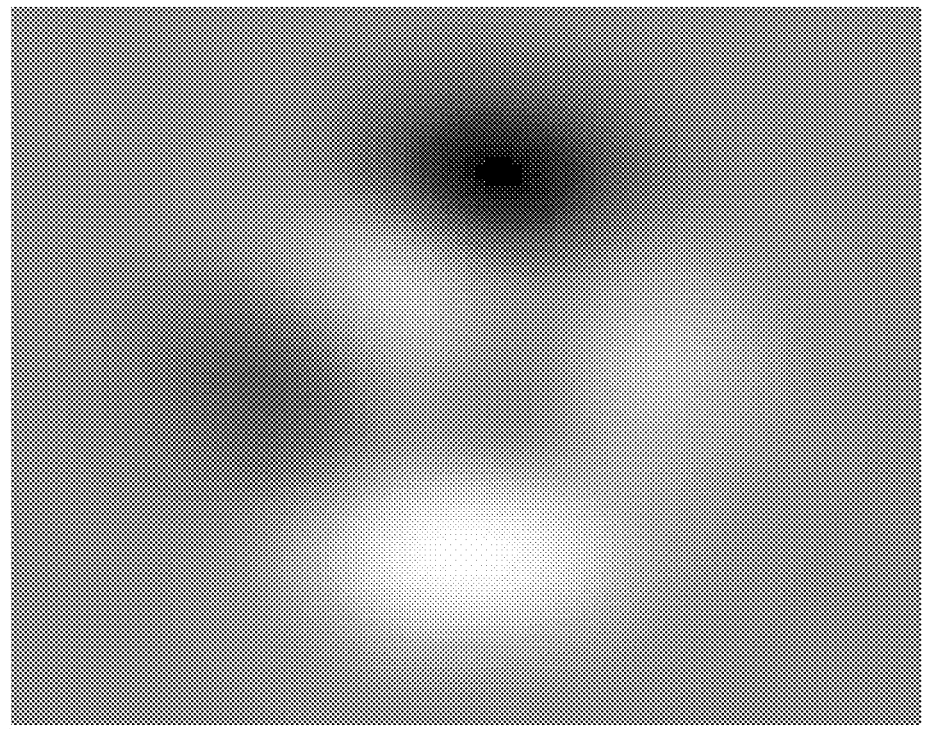
FIG. 8 shows according to an exemplary embodiment of the invention a two-dimensional spectroscopic map by sweeping both $f_c$ and $f_m$ in frequency. Each pixel of this map is obtained by extracting the detected pressure amplitude and phase at $2f_m$ at every swept $f_c$ and $f_m$. This map could be used to analyze composition and other properties of imaged object.

In the SFCW experiment, the envelope frequency is stepped from 50 kHz to 0.5 MHz in 5 kHz increments. The resulting TA signal has a doubled frequency of this envelope, with frequency steps of 10 kHz. Consequently the synthesized time window is 1/10 kHz=100 μs, corresponding to a maximum range of 15 cm. At each frequency step, the complex frequency response at the doubled envelope frequency is extracted. An inverse Fast Fourier Transform (FFT) was performed to synthesize the time/spatial response. FIG. 2A shows the spectrum of output TA signal with varying the excitation envelope frequency. We can see the peak at twice the envelope frequency. FIG. 2B shows the synthesized frequency response and time response. The arrows indicate the valleys of frequency response, which correspond to the destructive interference of the TA signals from top and bottom surfaces of the tissue sample. The generated stress wave from top and bottom boundaries will be in opposite directions and consequently destructive interference takes place if the tissue thickness is an integer multiple of the TA signal wavelength. Therefore, the valleys occur at $f=nv_s$/thickness, corresponding to 270 kHz, 405 kHz, and 540 kHz in this exemplary experiment. The thickness of the tissue can be calculated by 1500 m·s$^{-1}$/135 kHz=11.1 mm. The constructive interference occurs at frequencies $f=(2n+1)v_s/2$/thickness, which could also be observed as the peaks in the synthesized frequency response.

In the FMCW experiment, the transmitter sends out 200 μs long LFM signal with a repetition rate of 500 Hz. Depending on the type of application, the pulse length could be extended to several milliseconds or even longer. The envelope signal frequency sweeps from 0.1 MHz to 0.4 MHz shown in FIG. 3A. The matched filter response is a chirp with frequency sweep from 0.2 MHz to 0.8 MHz, as shown in FIG. 3B. The figure only shows the LFM signal and matched filter response within 100 μs for clarity. FIG. 3C shows the measured TA signal. FIG. 3D shows the correlation signal after the matched filter. A window function was applied to reduce side lobes. We can see there are two big peaks. They are from the top and bottom surfaces of the sample.

We performed a linear scan to get the cross section image of the tissue. The reconstructed images are shown in FIG. 4. The SNR was calculated by the peak value of TA signals divided by the standard deviation of the background noise signal. The calculated SNR for pulse TA with pulse width of 1 μs is 16 dB. For FMCW TA, the SNR of the received signal is 24.4 dB. The calculated SNR of FMCW correlation signal is 42.9 dB. Compared to the pulsed TA, the FMCW approach has a 26.9 dB SNR improvement. The SFCW TA method has an SNR of 33.2 dB, which is mainly limited by the available bandwidth.

Variations

Embodiments of the invention could be varied is different ways. For example, the microwave carrier $f_c$ and the modulation signal $f_m$ could both be swept in frequency. In another example, the acoustic pressures of an imaged object to different transmit signals could be recorded. In yet another example, the different responses could form a two-dimensional spectroscopic map, which could be used to analyze the composition and other properties of the imaged object. In still another example, frequency selective behavior (e.g. resonances) could occur in either the RF domain (due to complex dielectric response) or in the acoustic domain (e.g. from various absorption windows, resonances from boundaries, or other forms of standing waves). This approach could capture a two-dimensional plot of the response and fully characterize the target sample. This two-dimensional spectrogram could capture the following properties of the sample under test: RF/microwave characteristics, acoustic properties, thermoacoustic generation properties of various material and boundaries which itself depends on absorption, heating and heat capacity, expansion coefficients, which reveals mechanical and other characteristics of the target.

What is claimed is:

1. A thermoacoustic imaging device, comprising:
   (a) a transmitter configured to provide an electromagnetic transmit signal to an object being imaged, wherein the electromagnetic transmit signal has a carrier frequency $f_c$, and wherein the electromagnetic transmit signal is amplitude modulated at a modulation frequency $f_m$;
   (b) an acoustic detector configured to receive an acoustic signal from the object being imaged, wherein the acoustic signal includes a modulation term at $2f_m$ and a carrier term at $2f_c$, wherein the acoustic detector is responsive to the modulation term, wherein the carrier term cannot be detected by the acoustic detector, and wherein a non-linear thermoacoustic effect that doubles the modulation frequency $f_m$ in the object being imaged generates the acoustic signal from the object being imaged:
   wherein the transmitter transmits an interrupted modulated continuous-wave signal.

2. The thermoacoustic imaging device as set forth in claim 1, wherein the carrier signal is a continuous sinusoidal signal.

3. The thermoacoustic imaging device as set forth in claim 1, wherein the modulation signal is a continuous modulation signal.

4. The thermoacoustic imaging device as set forth in claim 1, further comprising a mixer for obtaining a continuous modulation signal.

5. The thermoacoustic imaging device as set forth in claim 1, further comprising a switch for obtaining an interrupted modulation signal.

6. The thermoacoustic imaging device as set forth in claim 1, wherein the modulation signal is a double-sideband fully suppressed-carrier modulation by multiplying the carrier signal $f_c$ with modulation signal $f_m$.

7. The thermoacoustic imaging device as set forth in claim 1, wherein the modulation signal comprises a form of pulse modulation.

8. The thermoacoustic imaging device as set forth in claim 7, wherein the pulse modulation is bipolar and the modulation is a double side-band fully suppressed-carrier modulation.

9. The thermoacoustic imaging device as set forth in claim 1, wherein $f_c$ is in the range of 100 MHz to 300 GHz and wherein $f_m$ is in the range of 20 kHz~100 MHz.

10. The thermoacoustic imaging device as set forth in claim 1, wherein the electromagnetic transmit signal is modulated at one or more further frequencies distinct from $f_m$.

11. The thermoacoustic imaging device as set forth in claim 1, further comprises a processing device configured for signal conditioning, for leakage and feed-through suppression, for coherent signal processing device, or for image reconstruction.

12. The thermoacoustic imaging device as set forth in claim 1, wherein the device is configured to further comprise a filtering device with a cutoff frequency in between $f_m$ and $2f_m$.

13. The thermoacoustic imaging device as set forth in claim 1, wherein the device is configured to further comprise a matching network for impedance matching of the transmit signal.

14. The thermoacoustic imaging device as set forth in claim 1, further comprising a coherent detection sub-system wherein the modulation of the electromagnetic transmit signal is derived from a transmit modulation frequency reference at $f_m$, wherein a receiver frequency reference at $2f_m$ is generated from the transmit modulation frequency reference via a second-order nonlinearity, and wherein coherent detection of the acoustic signal is performed using the receiver frequency reference.

15. The thermoacoustic imaging device as set forth in claim 1, further comprising a coherent detection sub-system wherein the modulation of the electromagnetic transmit signal is derived from a transmit modulation frequency reference at $f_m$, wherein a receiver frequency reference at $2f_m$ is generated from the transmit modulation frequency reference via a second-order nonlinearity, and wherein coherent detection includes use of a phase locked loop.

16. The thermoacoustic imaging device as set forth in claim 1, wherein the thermoacoustic imaging device is further configured to frequency sweep the modulation frequency $f_m$ and the carrier frequency $f_c$ for generating a two-dimensional spectroscopic map of the imaged object.

17. The thermoacoustic imaging device as set forth in claim 1, further comprising a processor configured to analyze the imaged object.

18. The thermoacoustic imaging device as set forth in claim 1, further comprising a processor configured for frequency correction of the received acoustic signal, calibration of the detector, or equalization of the received acoustic signal to compensate non-idealities in a frequency response of the detector.

* * * * *